United States Patent
Maynard

[11] Patent Number: 5,941,249
[45] Date of Patent: Aug. 24, 1999

[54] DISTRIBUTED ACTIVATOR FOR A TWO-DIMENSIONAL SHAPE MEMORY ALLOY

[76] Inventor: Ronald S. Maynard, 777 Hollebeck, #15Q, Sunnyvale, Calif. 94087

[21] Appl. No.: 08/756,099

[22] Filed: Nov. 25, 1996

Related U.S. Application Data

[63] Continuation-in-part of application No. 08/708,586, Sep. 5, 1996.

[51] Int. Cl.[6] .................................................. A61B 19/00
[52] U.S. Cl. .............................. 128/898; 623/1; 623/11; 623/12; 606/191
[58] Field of Search ................................... 128/898, 897; 623/1, 11, 12; 600/36; 606/191, 192, 194

[56] References Cited

U.S. PATENT DOCUMENTS

| | | | |
|---|---|---|---|
| 3,598,125 | 8/1971 | Cogley | 128/346 |
| 4,164,045 | 8/1979 | Bokros et al. | 3/1.4 |
| 4,337,090 | 6/1982 | Harrison | 148/402 |
| 4,490,975 | 1/1985 | Yaeger et al. | 60/527 |
| 4,524,343 | 6/1985 | Yaeger et al. | 60/527 |
| 4,533,411 | 8/1985 | Melton | 148/402 |
| 4,543,090 | 9/1985 | McCoy | 604/95 |
| 4,553,393 | 11/1985 | Ruoff | 60/528 |
| 4,559,512 | 12/1985 | Yaeger et al. | 337/140 |
| 4,565,589 | 1/1986 | Harrison | 148/402 |
| 4,601,705 | 7/1986 | McCoy | 604/95 |
| 4,631,094 | 12/1986 | Simpson et al. | 148/11.5 |
| 4,665,906 | 5/1987 | Jervis | 128/92 |
| 4,700,541 | 10/1987 | Gabriel et al. | 60/528 |
| 4,753,223 | 6/1988 | Bremer | 128/4 |
| 4,758,222 | 7/1988 | McCoy | 604/95 |
| 4,770,725 | 9/1988 | Simpson et al. | 148/402 |
| 4,776,541 | 10/1988 | Maynard | 244/165 |
| 4,777,799 | 10/1988 | McCoy et al. | 60/528 |
| 4,790,624 | 12/1988 | Van Hoye et al. | 350/96.26 |
| 4,884,557 | 12/1989 | Takehana et al. | 128/4 |
| 4,918,919 | 4/1990 | McCoy et al. | 60/528 |
| 4,990,883 | 2/1991 | Escobar et al. | 337/357 |
| 4,994,727 | 2/1991 | McCoy | 604/95 |
| 5,055,101 | 10/1991 | McCoy | 604/95 |
| 5,061,914 | 10/1991 | Busch et al. | 337/140 |
| 5,067,957 | 11/1991 | Jervis | 606/108 |
| 5,078,684 | 1/1992 | Yasuda | 604/95 |
| 5,090,956 | 2/1992 | McCoy | 604/95 |
| 5,114,402 | 5/1992 | McCoy | 604/95 |
| 5,135,517 | 8/1992 | McCoy | 604/281 |
| 5,165,897 | 11/1992 | Johnson | 434/113 |
| 5,176,544 | 1/1993 | Abujudom, II et al. | 439/878 |
| 5,188,111 | 2/1993 | Yates et al. | 128/657 |
| 5,190,546 | 3/1993 | Jervis | 606/78 |

(List continued on next page.)

FOREIGN PATENT DOCUMENTS

| | | | |
|---|---|---|---|
| 0 326 426 A2 | 8/1989 | European Pat. Off. | B29C 61/00 |
| 0 558 352 A1 | 9/1993 | European Pat. Off. | A61B 17/11 |
| 0 554 128 | 12/1993 | European Pat. Off. | F03G 7/06 |
| 61-185082 | 8/1986 | Japan . | |
| 61-190177 | 8/1986 | Japan . | |
| 3-5128 | 1/1991 | Japan . | |
| 7-75355 | 3/1995 | Japan . | |
| 7-247954 | 9/1995 | Japan . | |
| 1696298 | 12/1991 | U.S.S.R. . | |
| WO 90/15582 | 12/1990 | WIPO | A61F 2/06 |
| WO 92/01425 | 2/1992 | WIPO | A61F 2/06 |
| WO 94/19051 | 9/1994 | WIPO | A61M 37/00 |
| WO 95/34189 | 12/1995 | WIPO | H05B 3/00 |

Primary Examiner—Mickey Yu
Assistant Examiner—Dinh X. Nouyen
Attorney, Agent, or Firm—Wilson Sonsini Goodrich & Rosati

[57] ABSTRACT

An aneurism patch apparatus for treating an aneurism formed in a vessel includes a vessel interface side and an opposing non-interface side. A patch is formed of a sufficiently flexible material to provide a patch stowed state when the patch is delivered through the vessel and a patch deployed state when the patch is at least partially positioned over the mouth of the aneurism. The interface side of the patch is configured to form an adherence between the patch and an area of a vessel wall adjacent to the aneurism mouth. The adherence maintains a fixed position of the patch relative to the aneurism mouth.

9 Claims, 11 Drawing Sheets

U.S. PATENT DOCUMENTS

| | | | |
|---|---|---|---|
| 5,229,211 | 7/1993 | Murayama et al. | 428/424.4 |
| 5,254,130 | 10/1993 | Poncet et al. | 606/206 |
| 5,279,559 | 1/1994 | Barr | 604/95 |
| 5,309,717 | 5/1994 | Minch | 60/527 |
| 5,334,168 | 8/1994 | Hemmer | 604/281 |
| 5,335,498 | 8/1994 | Komatsu et al. | 60/528 |
| 5,345,937 | 9/1994 | Middleman et al. | 128/657 |
| 5,405,337 | 4/1995 | Maynard | 602/128 |
| 5,481,184 | 1/1996 | Jacobsen | 324/106 |
| 5,482,029 | 1/1996 | Sekiguchi et al. | 600/109 |
| 5,531,685 | 7/1996 | Hemmer et al. | 604/95 |
| 5,556,370 | 9/1996 | Maynard | 600/142 |
| 5,562,726 | 10/1996 | Chuter | 623/1 |
| 5,624,380 | 4/1997 | Takayama et al. | 600/146 |
| 5,662,621 | 9/1997 | Lafontaine | 604/281 |

DISTRIBUTED ACTIVATOR FOR A TWO-DIMENSIONAL SHAPE MEMORY ALLOY

CROSS-REFERENCE TO RELATED APPLICATIONS

This application is a continuation-in-part of Ser. No. 08/708,586, entitled "DISTRIBUTED ACTIVATOR FOR A TWO-DIMENSIONAL SHAPE MEMORY ALLOY", filed by Ronald S. Maynard on Sep. 5, 1996, incorporated herein by reference.

FIELD OF THE INVENTION

This application relates to a method and apparatus to treat an aneurism, and more particularly to a patch for treating an aneurism which is configured to form an adherence between the patch and an area of a vessel wall adjacent to an aneurism mouth and the adherence maintains a fixed position of the patch relative to the aneurism mouth.

BACKGROUND

There are several devices which exist that are used for the repair of aneurysms. U.S. Pat. No. 4,512,238 discloses a device for transluminal repair of, and restoring patency of, a weakened or damaged vessel uses a nitinol wire, previously memory-shaped into a straight wire and inserted into the vessel requiring repair. When placed in the body and stripped of heat insulation the wire warms and returns to a preselected coiled dimensions to support the vessel wall. One problem with this device is the difficult task of attaching a sleeve to the wire support because the wire is many times longer than the sleeve at the time it is inserted.

U.S. Pat. No. 4,140,126 discloses another device for repairing an aneurism. The device is mounted on the outside of a carrier catheter and is positioned in the vessel in a collapsed form, smaller in diameter that of the vessel. The device is then expanded onto the vessel well by the use of a separate mechanical expanding apparatus which is controlled by the user from outside the body.

U.S. Pat. No. 4,787,899 describes a system of positioning a graft within a body lumen. The graft is loaded into a guide which is inserted into the lumen. An inflatable balloon is used to anchor the distal end of the graft onto the wall of the lumen. The guide is then pushed upstream, pulling the folded graft out of the guide and onto the wall of the lumen where staples end anchor it into the wall of the lumen. One problem with this device is that the balloon providing the anchor for the distal end of the graft while the guide is moved upstream may not provide enough pressure on the wall of the vessel to prevent slippage which could result in misplacement of the graft.

It would be desirable to provide an aneurism patch which does not have a coil configuration and which adheres to the vessel wall adjacent to the mouth of the aneurism. It would be further desirable to provide an aneurism patch which has non-electrically activated deployed state configured to be positioned adjacent to the mouth of the aneurism. Yet it would still further desirable to provide an aneurism patch which has an electrically activated deployed state that is configured to be positioned adjacent to the mouth of the aneurism.

SUMMARY OF THE INVENTION

An object of the invention is to provide a method and apparatus for treating aneurysms.

Another object of the invention is to provide an aneurism patch which is positioned over a mouth of an aneurism.

Still another object of the invention is to provide an aneurism patch which has a non-electrically deployed state that is positioned over a mouth of an aneurism.

Yet another object of the invention is to provide an aneurism patch which is introduced into a vessel in a stowed state and is positioned over the mouth of the aneurism in a deployed state.

A further object of the invention is to provide an aneurism patch with a vessel interface side that includes a plurality of anchor elements.

Still another object of the invention is to provide an aneurism patch forms a mechanical adherence between the patch and the vessel wall adjacent to the aneurism mouth.

Yet another object of the invention is to provide an aneurism patch with an aperture configured to be coupled to a low pressure source.

Another object of the invention is to provide an aneurism patch at least partially made of a material with an internal stress and a pre-defined shape, where the internal stress moves the patch from a stowed state to the pre-defined state.

Still another object of the invention is provide an aneurism patch that is formed of a thermally active material that moves to a pre-defined shape when electrically heated.

A further object of the invention is to provide an aneurism patch which is made of a shape memory alloy (SMA) element with an activation threshold greater than body temperature.

These and other objects of the invention are achieved in an aneurism patch apparatus for treating an aneurism formed in a vessel includes a patch with a vessel interface side and an opposing non-interface side. The patch is formed of a sufficiently flexible material to provide a patch stowed state when the patch is delivered through the vessel and a patch deployed state when the patch is at least partially positioned over the mouth of the aneurism. The interface side of the patch is configured to form an adherence between the patch and an area of a vessel wall adjacent to the aneurism mouth. The adherence maintains a fixed position of the patch relative to the aneurism mouth.

In one embodiment of the invention the patch includes a vessel interface side and an opposing non-interface side, the patch is configured to have a stowed state when delivered to a mouth of the aneurism. The patch is formed of a thermally active material that moves to a pre-defined shape when electrically heated. The pre-defined shape forms an adherence between the vessel interface side and an area of the vessel all adjacent to the aneurism mouth. The adherence maintains a fixed position of the patch relative to the aneurism mouth.

DETAILED DESCRIPTION OF THE INVENTION

The present invention provides an aneurism patch apparatus for treating an aneurism formed in a vessel which includes a patch with a vessel interface side and an opposing non-interface side. The patch is formed of a sufficiently flexible material to provide a patch stowed state when the patch is delivered through the vessel and a patch deployed state when the patch is at least partially positioned over the mouth of the aneurism. The interface side of the patch is configured to form an adherence between the patch and an area of a vessel wall adjacent to the aneurism mouth. The adherence maintains a fixed position of the patch relative to the aneurism mouth.

In one embodiment of the invention, the patch assumes the deployed state passively and is not electrically activated.

In another embodiment, of the invention the patch is formed of a thermally active material that moves to a pre-defined shape when electrically heated. The pre-defined shape/deployed state forms the adherence between the vessel interface side and an area of the vessel wall adjacent to the aneurism mouth. In the pre-defined shape/deployed state, the patch has a circumference that is less than 360 degrees, more preferably less than 240 degrees and still more preferably less than 180 degrees. In the pre-defined shape/deployed state patch can have an interface side that is in substantial conformance (curvature) with the geometry of the adjacent vessel wall.

Passive activation of the patch is achieved with a spring force that is inherent to the patch. This spring force can then drive one or more adhesive devices into the wall of the vessel surrounding the aneurism. Adhesion is achieved either by selecting materials for the patch which have internal spring forces, including SMA's and bimorphs, or with adhesion devices positioned on an interface surface of the patch to the vessel wall. Adhesion is non-frictional.

Figure 1:
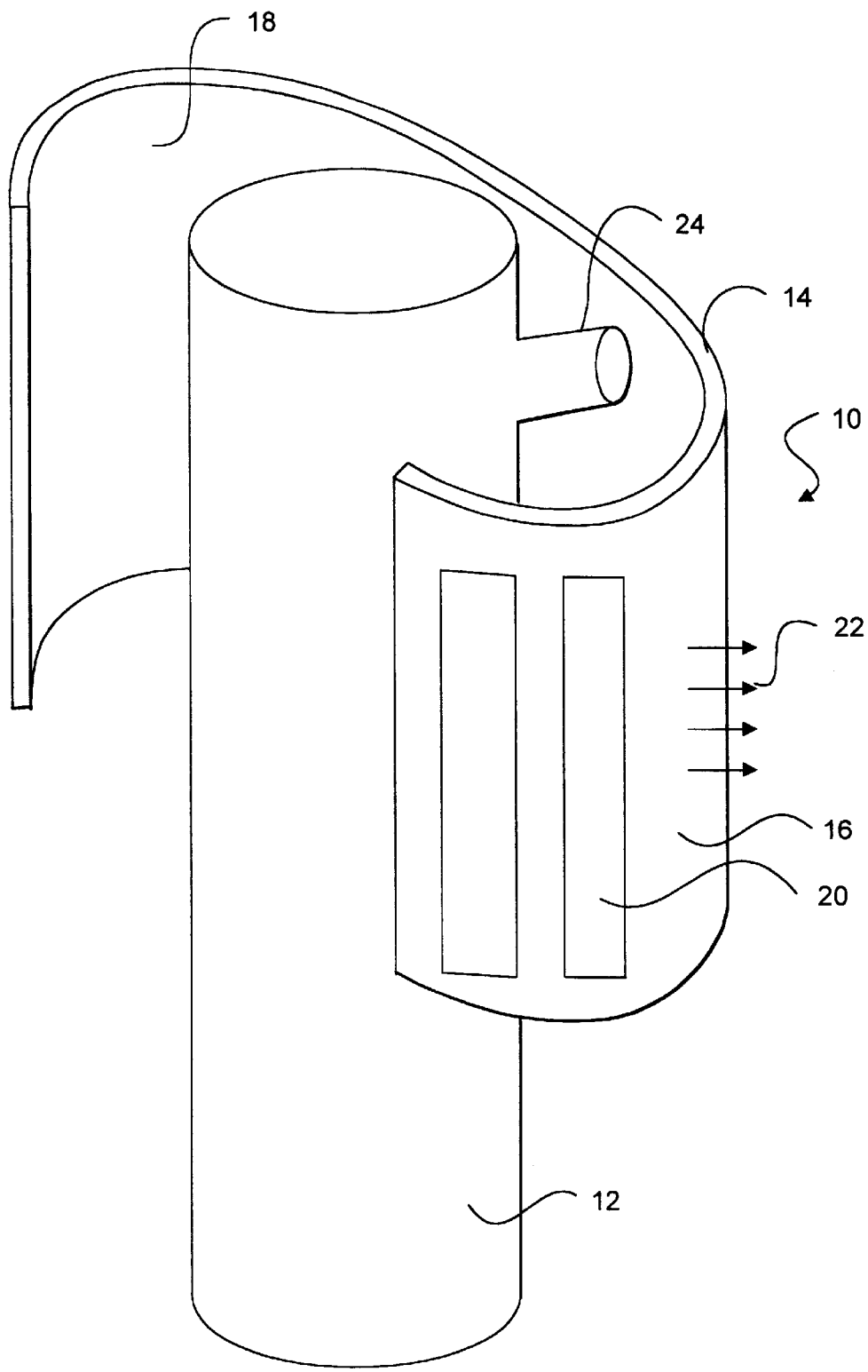
FIG. 1 is a perspective of an aneurism patch apparatus of the present invention.

Referring now to FIG. 1, aneurism patch apparatus is denoted as 10 and optionally includes a delivery device, including but not limited to a catheter 12. A patch 14 is illustrated in a deployed state or in a pre-defined shape. Patch 14 has an interface surface 16 and an opposing non-interface surface 18. In one embodiment, an adhesive is at least partially positioned on interface surface 16. Patch 14 can be formed of a flexible material that is porous or non-porous and can include a stent type of geometry as well as a mesh. In one embodiment, one or more mechanical adhesion devices 22 are positioned on interface 16 are become at least partially positioned in the vessel wall in which the aneurism is formed. Suitable mechanical devices 22 include but are not limited to the application of a vacuum or a low pressure source, barbs, hooks graspers, pinchers and the like.

When a vacuum is applied adhesion devices 22 are forced into the surface of the vessel wall surrounding the aneurism mouth and anchor aneurism mouth down. When patch 14 is porous a compliant shape is desirable between interface surface 16 and the vessel wall surrounding the aneurism mouth. Additionally, with a porous patch 14 a spring force inherent in patch 14 is used to drive adhesion devices 22 into the vessel wall. Other mechanical devices including but not limited to a balloon coupled to cannula 12 can be used to apply pressure on interface surface 16 and adhesion devices 22. Patch 14 provides an internal force the area of the vessel adjacent to the aneurism. This force can be activated by thermal energy or mechanical energy inherent and/or applied to patch 14. A releasable connector 24 couples patch 14 to catheter 12.

Figure 2:
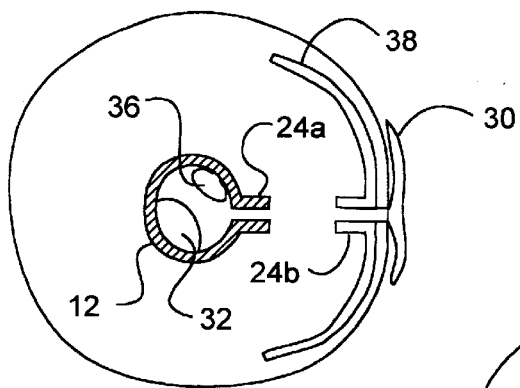
FIG. 2 is a cross-sectional view of the patch of FIG. 1 positioned adjacent to an aneurism.

Referring now to FIG. 2, patch 14 includes an aperture 26 that is configured to positioned over the mouth of the aneurism. In one embodiment, connector 24 includes a catheter connector 24*a* and a patch connector 24*b*. Connectors 24*a* and 24*b* provide a mechanical release of patch 14 from catheter which can be a shape memory alloy (SMA) element, devices that when activated pinch off a catheter lumen from patch 14 can sever the two with a loop of wire or a heated wire that when pulled can cut, or an actual fabricated joint which is a release mechanism such as a catch. The SMA element can have an activation threshold greater than body temperature.

Figure 3:
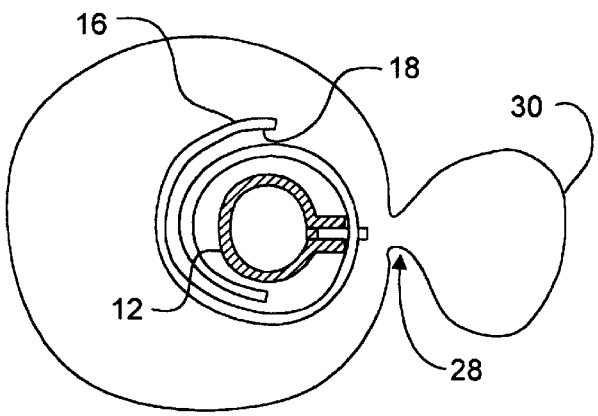
FIG. 3 is a cross-sectional view of a patch positioned on an exterior surface of a catheter when the patch is in a stowed position.
Figure 4:
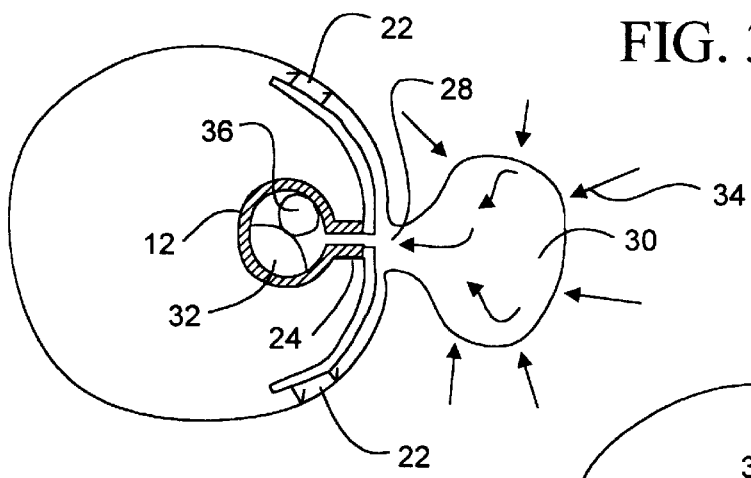
FIG. 4 is a cross-sectional view of the patch in a deployed position and the evacuation of the aneurism through a lumen formed in the catheter.
Figure 5:
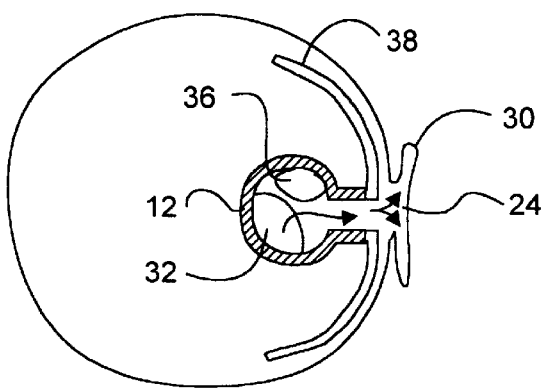
FIG. 5 is a cross-sectional view of the patch in a deployed/pre-shaped position, the introduction of an adhesion medium and the collapse of the aneurism.

FIG. 3–FIG. 5 illustrate the positioning and release of patch 14 at aneurism mouth 28. In FIG. 3, patch 14 is in the stowed state and positioned on an exterior of catheter 12. In other embodiments, patch 14 can be positioned in an interior of catheter 12, and at a distal end of catheter 12. In the stowed state, the surface area of patch 14 is minimized to achieve access to aneurism mouth 28 for the treatment of aneurism 30.

As illustrated in FIG. 4, patch 14 is in its deployed or pre-shaped state. Aperture 26 is positioned substantially over aneurism mouth 28. Catheter 12 is shown as having a catheter lumen 32 which provides for evacuation of aneurism 30 when catheter lumen 32 is coupled to a low pressure source, including but not limited to a vacuum source. Aneurism 30 is at a lower pressure than the rest of the of the vessel wall. Pressure 34, as shown with the arrows, is applied to aneurism 30, creating the possibility of creating a bursting of aneurism 30. Coupling aneurism 30 to a low pressure source with catheter lumen 32 begins an evacuation of aneurysm 30. Patch 14 can include an SMA including but not limited to NiTi, a micro-fabricated circuit, a micro-fabricated sensor and a micro-fabricated transducer. Suitable micro-fabricated sensors include pressure, temperature, electrosonic, voltage potential, chemical, chemical potential and electronic magnetic sensors. Suitable micro-fabricated transducer include temperature, electrosonic, voltage potential and electromagnetic transducers. Patch 14 can have a one-way of two-way shaped memory effect.

Figure 6:
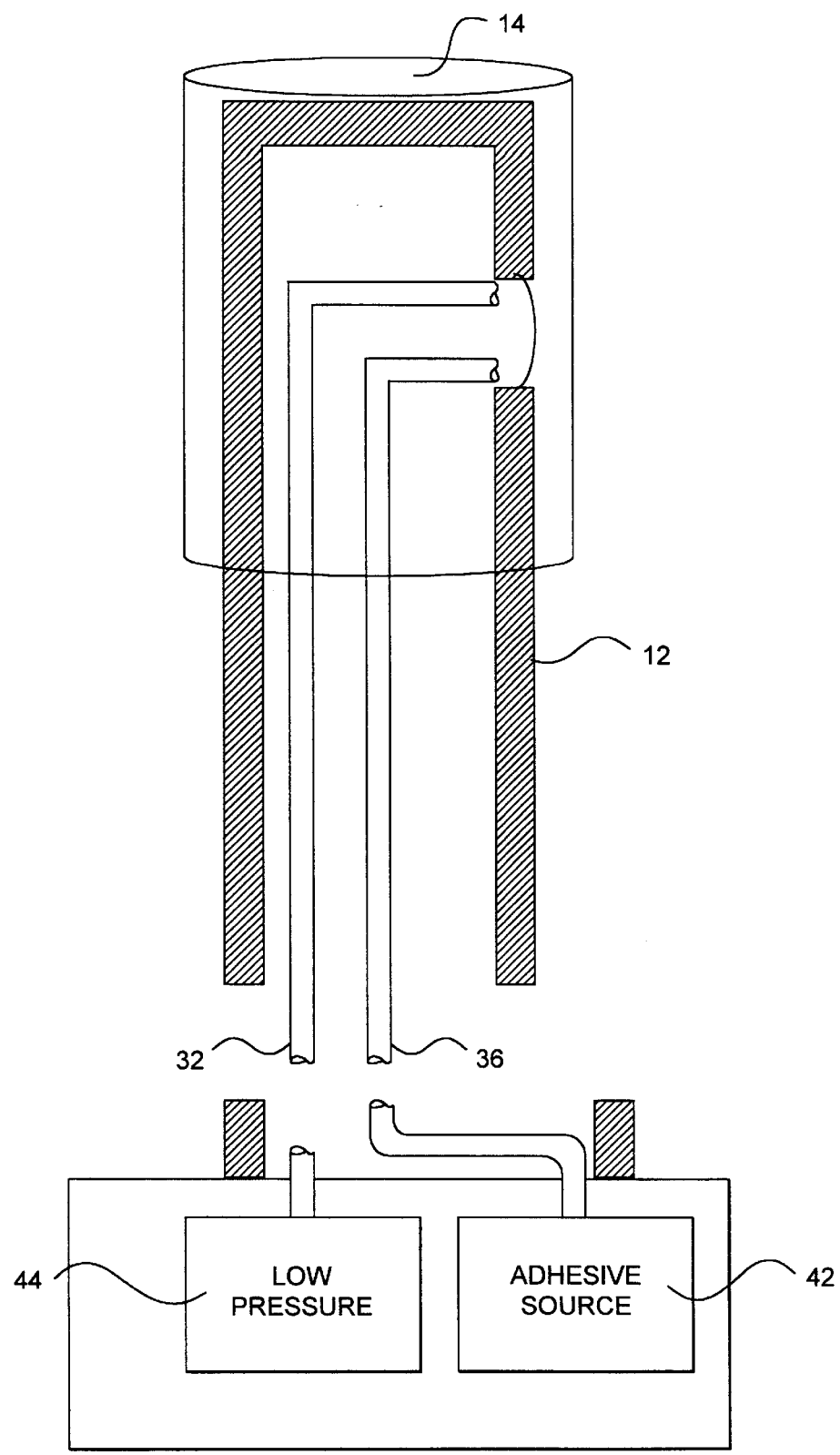
FIG. 6 is a cross-sectional view of the stowed patch positioned at a distal end of the catheter.

FIG. 5 shows aneurism 30 fully collapsed. After aneurism 30 is collapsed, adhesive can be introduced through an introduction lumen 36. Introduction lumen 36 is coupled to a source of adhesive or other material of interest that can retain aneurism 30 in a contacting position with interface surface 16. Such adhesives such as cyanacrylates, as known to those skilled in the art. Adhesive can partially or fully fill an interstitial area 40, which is the volume occupied between the interface surface 16 the surface of the vessel wall. Adhesive can take up any irregularities between the vessel wall and interface surface 16. The use of the adhesive is optional to provide a complete or a partial contacting relationship between interface surface 16 and the vessel wall. The blood within the vessel is applying pressure. FIG. 6 illustrates an adhesive source 42 coupled to introduction lumen 36 and a low pressure source 44 coupled to catheter lumen 32.

Figure 7:
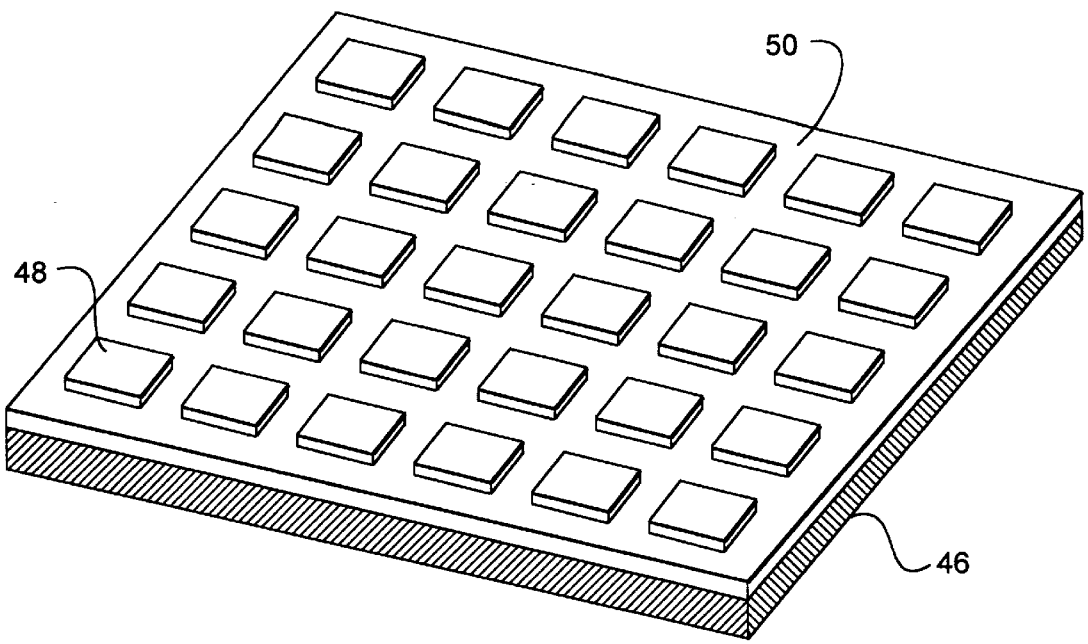
FIG. 7 is an isometric view of a deactivated two-dimensional sheet according to the invention.

The following discussion pertains to a suitable material for patch 14 which is an SMA material or a bimorph. A simplified embodiment of a two-dimensional sheet 46 according to an aspect of the invention is shown in FIG. 7. The basic concepts discussed here can be applied directly to practical embodiments which will be described later. In this case sheet 46 is made entirely of a SMA chosen from the group of electrically conductive materials. Most common examples include NiTi alloys and CuZnAl alloys. Other alloys can also be used. The ratio of the thickness of sheet 46 to the lateral extent of heating element 48 should be preferably as small as possible, while still capable of maintaining the integrity of sheet. SMA sheet 46 is produced by a variety of common machining methods; such as rolling of thin foils from wire or thin plate stock, sectioning thin wafers from bar stock, or like methods. At present, sectioning of thin wafers from bar stock is preferred. Wafers of SMA material may be sliced from bar stock using a conventional band saw, a cold saw, an annular diamond wet saw, or electro-discharge machining (EDM) or like methods. The resulting wafer can be heat treated to a flat condition and precision-ground to any desired thickness. SMA bulk properties are assured as the material is obtained directly from bulk. The SMA material contained in sheet 46 can be pre-trained prior to assembly or left untrained. The choice depends on the eventual application.

A plurality of heating elements 48 are positioned on top of SMA sheet 46 and insulated from sheet 46 by an electrically insulating layer 50. It is most convenient to laminate or otherwise deposit electrically insulating layer 50 on sheet 46. Electrically insulating layer 50 prevents current leakage between heating elements 48 and electrically conducting sheet 46. Electrically insulating layer 50 also preferably is a good thermal conductor. Preferred insulating materials include polyimide or silicon nitride $Si_xN_y$. The thickness of electrically insulating layer 50 should be small in relation to its lateral extent. For example, electrically insulating layer 50 may be a 2000 Å silicon nitride layer to ensure adequate thermal coupling, and to ensure thermal conductivity between heating elements 48 and sheet 46. In the simplified embodiment of FIG. 7, heating elements 48 are in the form of thin-film resistors. Most preferably, heating elements 48 are ohmic heaters or other similar devices capable of converting electrical current to thermal energy. They can comprise any conventional resistive material such as TiW or TaO. Conveniently, the resistive material is first deposited and patterned on layer 50 by well known VLSI or micro-machining techniques. Then, heating elements 48 are patterned or otherwise formed according to well-known techniques.

Figure 8:
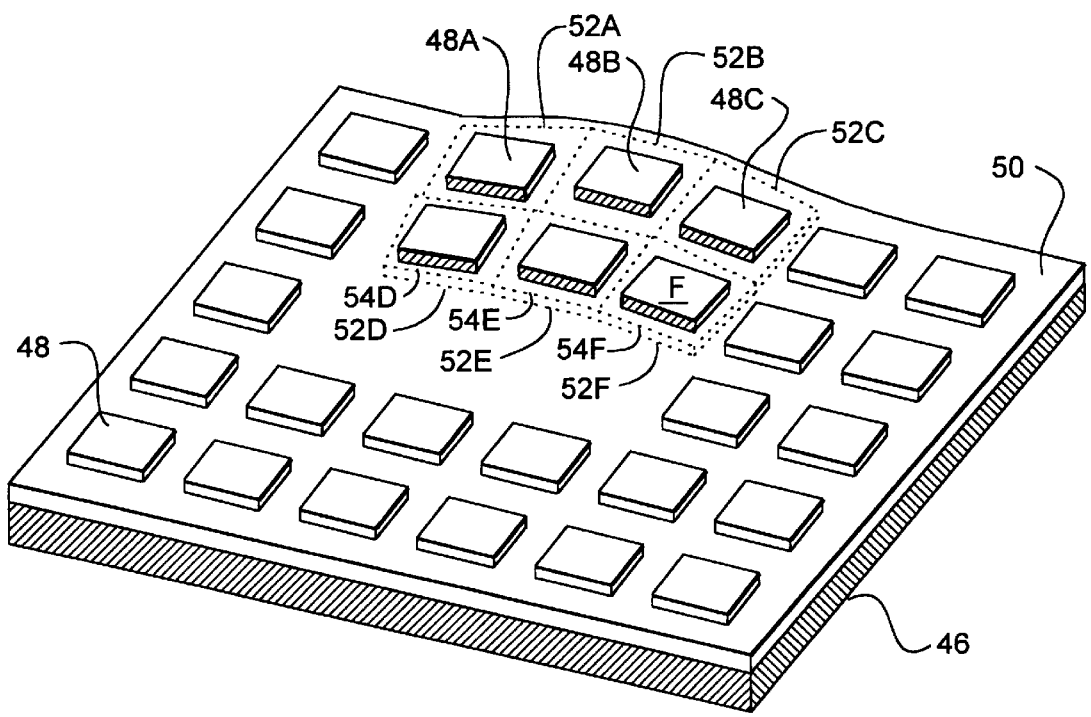
FIG. 8 is an isometric view of the two-dimensional sheet of FIG. 7 in the activated state.

The operation of the simplified embodiment is best understood by comparing FIG. 7–FIG. 8. In this case, the SMA material has been pre-trained to assume a predetermined shape when thermally activated to an activation threshold temperature. In FIG. 7, SMA sheet 46 is shown in an inactive state. FIG. 8 shows a particular case wherein six heating elements 48, labeled as 48A–F, are providing heat. Consequently, the heat traverses section 54A–F of insulating layer 50 and causes adjacent portions 52A–F of SMA sheet 46 to reach activation threshold. As a result, portions of 52A–F assume a well-defined shape and in the process, provide useful activation forces. As shown, the local deformation is upward convex. Once portions 52A–F assume their shape, the areas of sheet 46 surrounding those portions deform in accordance with a predetermined memory characteristic. In fact, entire sheet 46 assumes a resultant shape due to local changes as dictated by its geometry. In the simple case of FIG. 8, the remainder of sheet 46 remains flat or otherwise returns to its neutral shape; neutral meaning its inactive state. More complex resultant shapes will be described in later embodiments.

Figure 9:
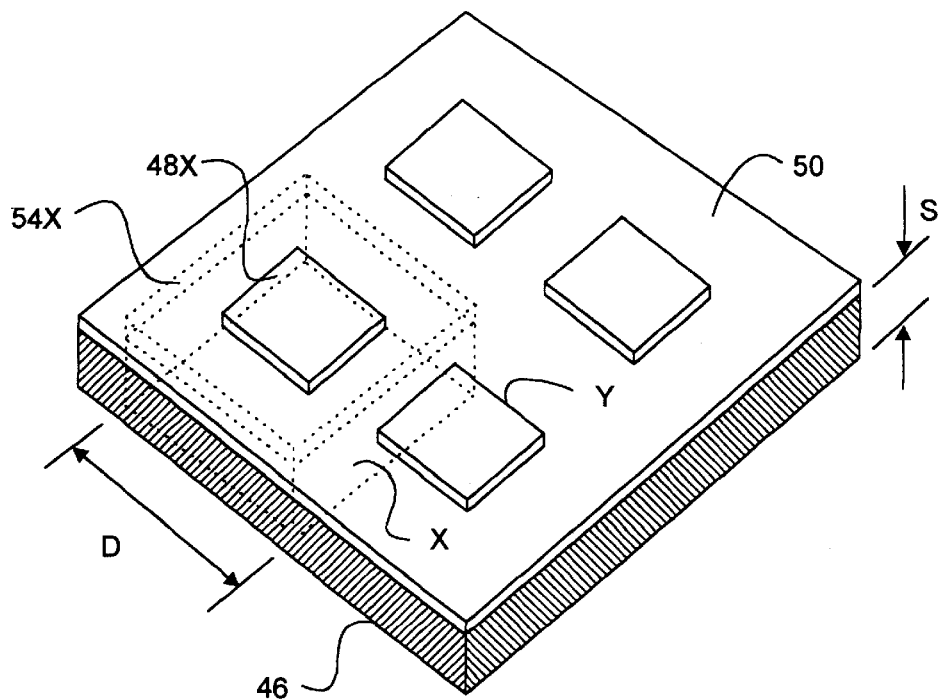
FIG. 9 is an isometric view of a portion of the two-dimensional sheet of FIG. 7.

In FIG. 9 the thickness of sheet SMA 46 is labeled by S. For clarity, a particular heating element 48X has been selected to explain the details of the invention. Heating element 48X has associated with it an adjacent portion 52X of SMA sheet 46. As shown, heating element 48X has associated with it a section 54X of electrically insulating layer 50 as well. Portion 52X is located directly underneath heating element 48X. The width of portion 52X is denoted by D. As shown, heating element 48X provides heat to portion 52X exclusively. Heat propagates through section 54X and into section 52X which represents a localized portion of SMA sheet 46.

Figure 10A:
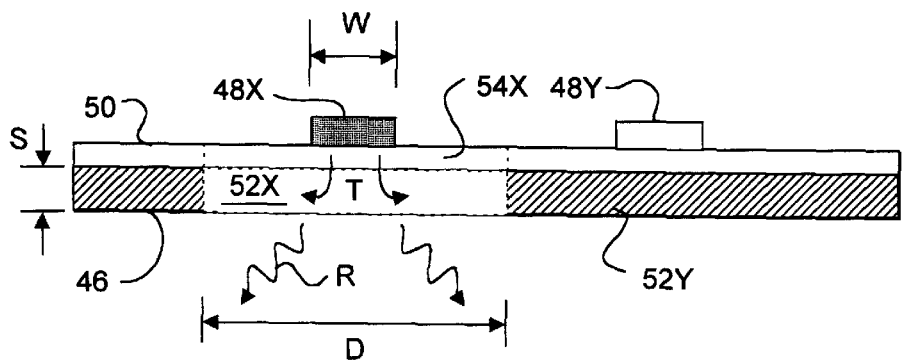
FIG. 10A is a cross-section of the portion of the two-dimensional sheet of FIG. 9.

The principles behind the heating process and the shape assumed by adjacent portions 52 are best illustrated in FIG. 10A. We consider one heating element 48X. For clarity, the predetermined shape assumed by adjacent portion 52X upon heating has not been shown. The heat generated by element 48X, whose width is indicated by W, passes along arrows through insulating layer 50. In particular, the thermal energy traverses section 54X of layer 50. Layer 50 is proportionally very thin compared to the lateral dimensions, and thus section 54X readily transfers the heat to sheet 46. Once in sheet 46 the heat propagates throughout adjacent portion 52X.

Figure 10B:
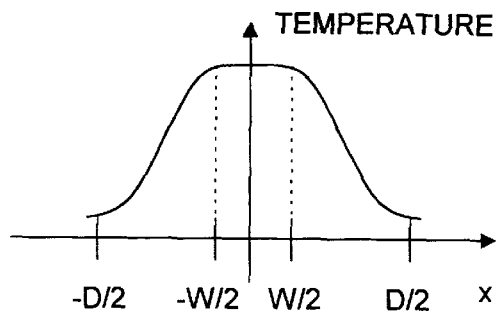
FIG. 10B is a graph of the temperature distribution in the portion of FIG. 10A.

The graph in FIG. 10B represents temperature distributions at an arbitrary fixed depth below heater 48X, and shows the temperature distribution laterally, in the X direction, inside portion 52X. Directly under element 48X the temperature remains at a maximum, as indicated by the flat portion of the curve from −W/2 to +W/2. In other words, the heat delivered to portion 52X does not propagate to other portions, e.g., portion 52Y. Instead, the heat radiates along arrows R out of sheet 46 before reaching other portions 52Y.

Figure 11:
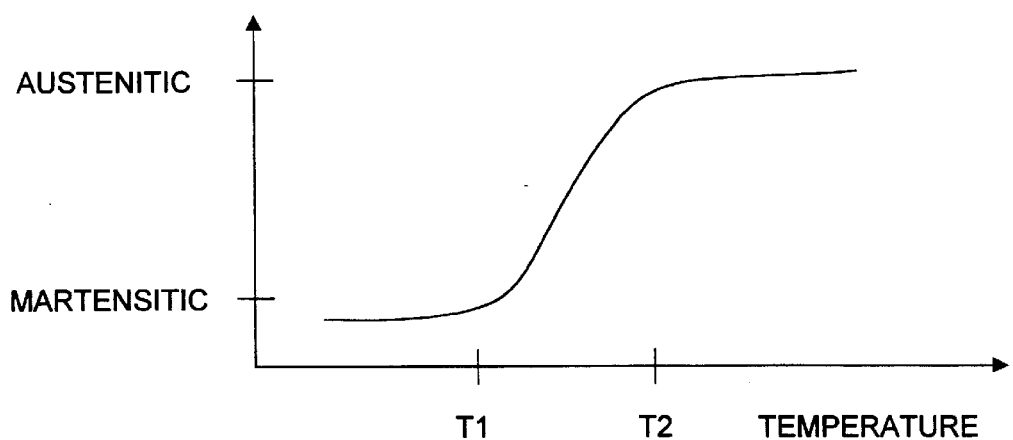
FIG. 11 is a graph of the transition between the martensitic and austenitic states as a function of temperature.

As already mentioned, the shape of adjacent portions 52 depends on the pre-trained shape of the SMA or sheet 46 in those regions. Also, the shape depends on the temperature maintained in portions 52. Full conformity to the pre-trained shape is achieved when the temperature in portions 52 is equal or higher than the critical i temperature at which the SMA material attains the austenitic state. This is best shown in the graph of FIG. 11. At temperatures below $T_1$ the SMA material remains pliable, as dictated by the martensitic properties. Therefore, portions 52 maintained at or below $T_1$ will conform to the shape imparted to them by the surroundings. The transition to the austenitic state occurs between temperatures $T_1$ and $T_2$. When portions 52 are kept in this temperature range they will assume an intermediate shape between the relaxed and pre-trained forms. Careful thermal regulation thus allows one to vary the shape of any portions 52 of sheet 46 in a continuous manner. The overall structure of sheet 46 where heating elements 48 are mounted directly on sheet 46 with only layer 50 interposed between them is very simple. The assembly process is straightforward and low-cost.

Figure 12:
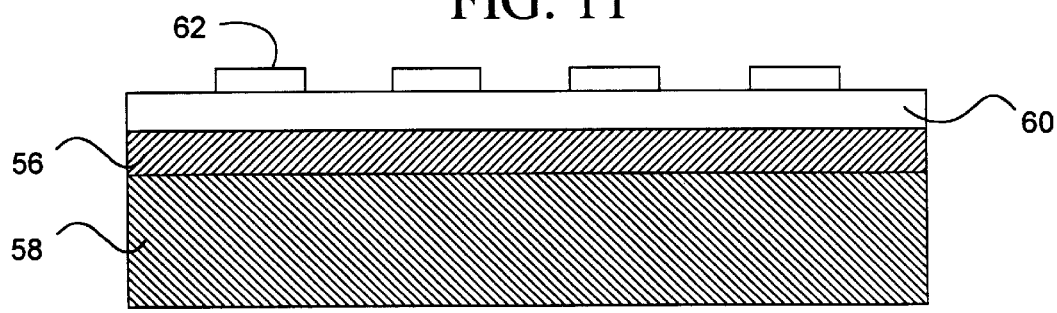
FIG. 12 is a cross-section of a two-dimensional sheet with an insulating layer and a coating layer.

Another embodiment of the invention is shown in FIG. 12. Here, a two-dimensional sheet 56 of SMA material is placed on a coating layer 58. In this case, layer 58 is sufficiently thick to provide mechanical stability. A thin insulating layer 60 is disposed on top of sheet 56 to provide electrical insulation between heating elements 62 and sheet 56. Layer 60 is thin enough and has appropriate thermal properties to permit the free flow of heat from elements 62 to sheet 56. In this embodiment the SMA material of sheet 56 is also electrically conducting (e.g., TiNi alloy or CuZnAl alloy). The operation of this embodiment is analogous to the operation of the first one. The added stability of coating layer 58 ensures conformity to a well-defined shape when all portions of sheet 56 are in the martensitic state.

Figure 13:
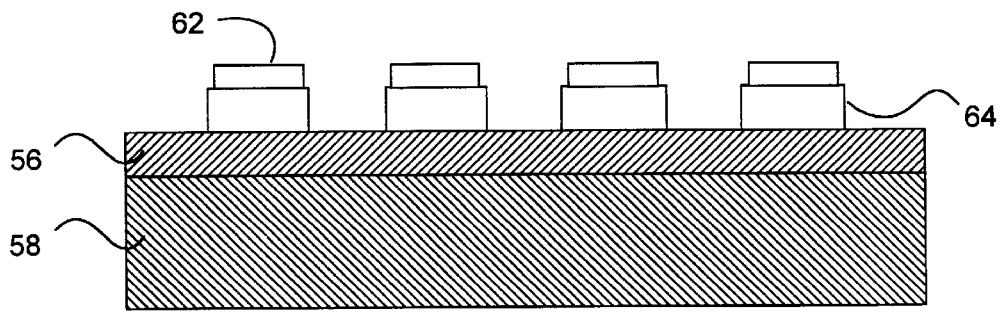
FIG. 13 is a cross-section of a two-dimensional sheet with point-wise applied insulating layer and a coating layer.

The embodiment of FIG. 13 exhibits sheet 56 of electrically conducting SMA with a coating layer 68 acting as substrate. In this case layer 68 is chosen from materials which are chemically inert and stable to protect sheet 56 from adverse effects. Electrical insulation between heating elements 62 and sheet 56 is provided by sections of electrical insulation sections 64 deposited point-wise under elements 62. Such structure can be produced by initially applying a layer of insulating material and a layer of heating material. Then, elements 62 and a corresponding electrical insulation sections 64 are fashioned by etching or another well-known process. Preferably, a well known VLSI technique or a micro-machining technique is employed for this purpose.

Figure 14:
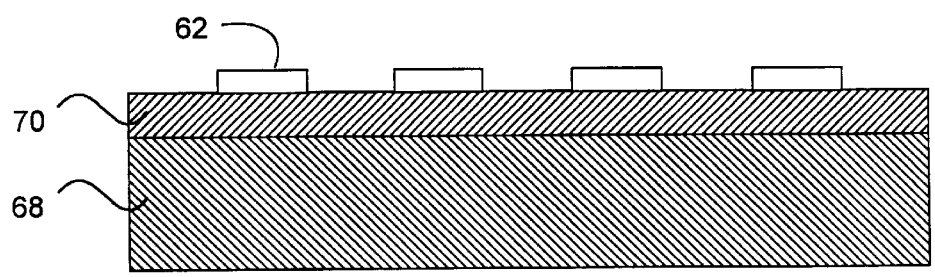
FIG. 14 is a cross-section of a two-dimensional sheet with a coating layer.

FIG. 14 shows yet another embodiment in which a two-dimensional sheet 70 is made up of an electrically insulating SMA material. In this configuration no insulation is necessary. Consequently, heating elements 62 are mounted directly on sheet 70. A coating layer 68 functioning as substrate is once again provided to afford mechanical stability and resistance. It is preferable that layer 68 also be a good thermal conductor to aid in the dissipation of heat from sheet 70. The embodiments of FIG. 12–FIG. 14 all operate in the manner set forth above. The modifications introduced are intended to aid one skilled in the art in selecting the appropriate structure given a set of technical requirements.

Figure 15:
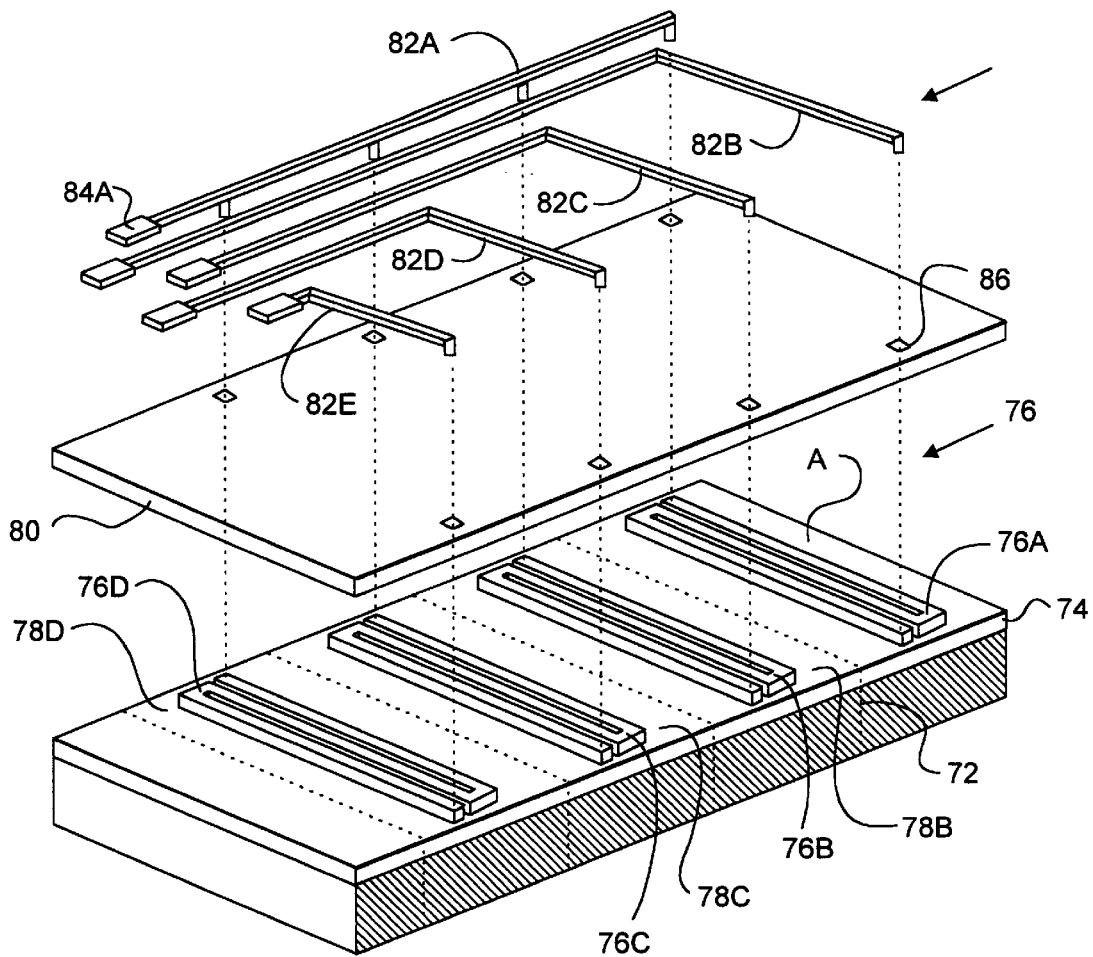
FIG. 15 is an exploded view illustrating the assembly of a two-dimensional sheet and the activation elements according to the invention.

A preferred embodiment is shown in FIG. 15. A two-dimensional sheet 72 of an electrically conducting SMA material, preferably a NiTi alloy is coated with insulating layer 74. Preferably, layer 74 is made of $Si_xN_y$ or polyimide and is sufficiently thin to readily conduct heat. Patterned heating elements 76A–D are located on layer 74. Elements 76A–D are obtained by first sputtering TiW or TaO on top of layer 74 and then performing a patterning step. Heating elements 76A–D offer a very high resistance. In the preferred embodiment elements 76A–D have a zig-zag shape. This enables them to ensure better heat distribution in sheet 72 when active.

A second insulating layer 80 is provided on top of elements 76A–D and layer 74. Preferably, layer 80 is made of a flexible electrical insulation such as polyimide, which can be spun coated onto elements 76A–D and layer 74. A number of through-holes 86 are opened in layer 80 to permit electrical contact with elements 76A–D. Holes 86 are sensibly aligned with the terminal portions of elements 76A–D. A set of conduction lines 82A–E are patterned on top of layer 80. Preferably, conduction lines 82A–E are made of a flexible and highly conductive material such as gold. Lines 82A–E can be defined by patterning or other suitable techniques. A common return line 82A is laid out to provide electrical contact with the left terminals of all elements 76A–D. Return line 82A saves surface area of top of layer 80 and is desirable as long as all elements 76A–D are not addressed simultaneously on a continuous basis. If continuous activation is required, then an additional full width layer would be dedicated for the return path. The other lines, 82B–E are in electrical contact with the right terminals of elements 76A–D respectively. External electrical connections are made to contact pads 84A–E, corresponding to lines 82A–E. For this purpose, pads 84A–E are designed much thicker than lines 82A–E. The actual electric connections are made with wire bonding or similar means.

Once the entire structure on sheet 72 is assembled, the SMA is "trained" by forcing sheet 72 to assume a resultant shape using well-known methods. For example, sheet 72 is formed on a mandrel and fixed in place with a clamp. The entire fixture is then placed in an annealing furnace, preferably purged with an inert gas, at approximately 450 C. for about 30 minutes. Upon cooling the film is released from the mandrel. At this time sheet 72 is operationally ready.

Figure 16:
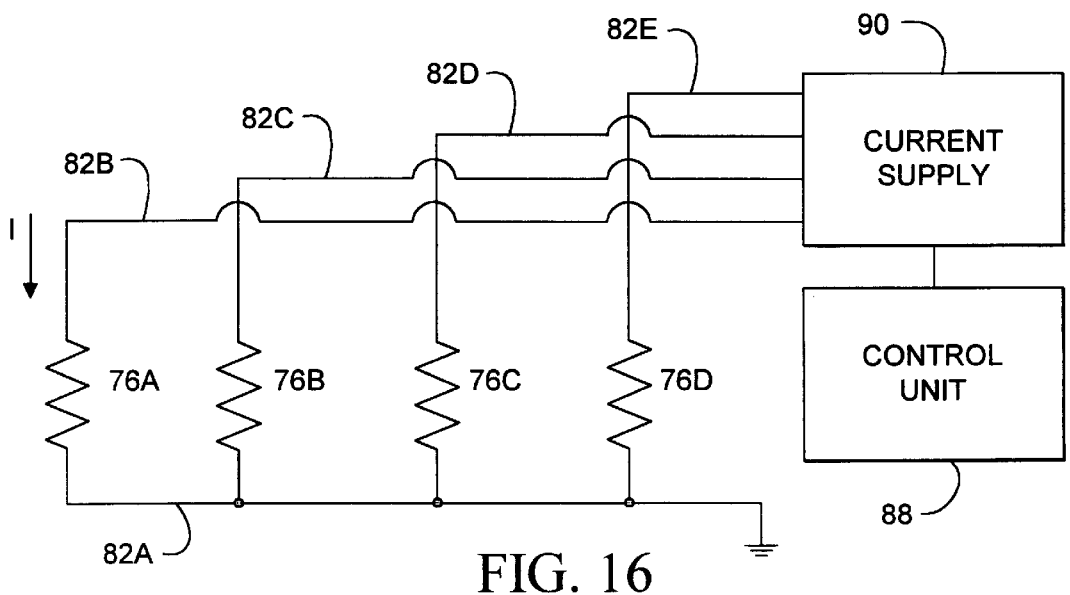
FIG. 16 is a diagram showing the equivalent circuit of the activation mechanism.

The electrical diagram showing the electrical connections of the preferred embodiment is found in FIG. 16. A control unit 88 is connected to a current supply 90. Preferably, both unit 88 and supply 90 are located away from sheet 72. Unit 88 is preferably a micro-processor capable of selecting a desired combination of elements 76. Current supply 90 is preferably an adjustable source capable of delivering current to the selected combination of elements 76. Lines 82B–E are connected directly to supply 90. Elements 76A–D are shown as resistors. Return line 82A is grounded.

During operation control unit 88 selects a combination of elements to be activated. It then sends a corresponding command to supply 90. Supply 90 responds by delivering current to elements of the chosen combination. For example, elements 76A and 76D are chosen. Current is delivered to elements 76A and 76D and the corresponding adjacent portions 78A and 78D assume a well-defined shape. If the current is sufficiently large and the temperature maintained in adjacent portions 78A and 78D is above $T_2$ (see FIG. 11)

then portions 78A and 78D will assume their pre-trained shape. If the temperature is between $T_1$ and $T_2$ portions 78A and 78D will assume an intermediate shape. Because supply 90 is adjustable the proper current can be selected during operation and adjusted on an empirical basis. Consequently, the shape of portions 78A and 78D can be varied as necessary.

Figure 17:
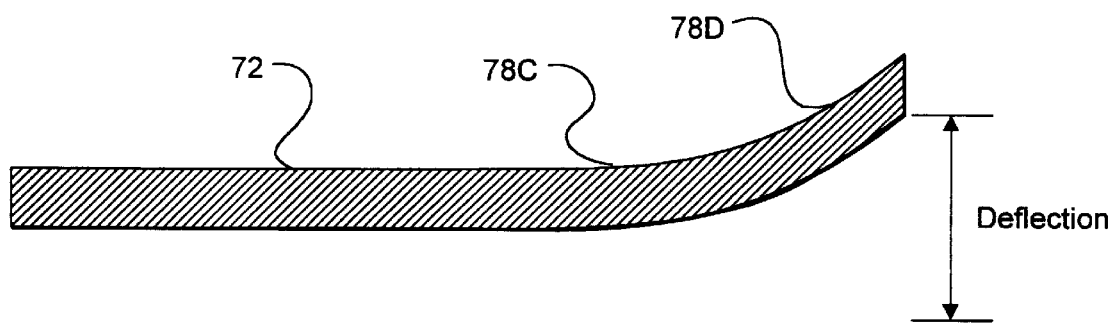
FIG. 17 is a side view illustrating the deflection of a two-dimensional sheet according to the invention.
Figure 18:
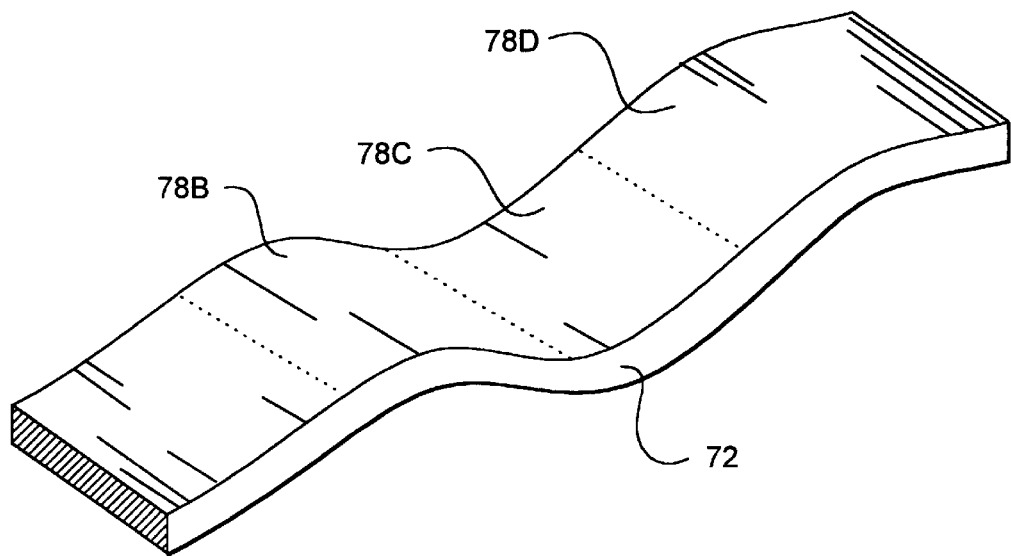
FIG. 18 is a perspective view illustrating a complex pre-trained shape of a sheet according to an aspect of the invention.

FIG. 17 illustrates the resultant shape of sheet 72 when adjacent portions 78C and 78D are selected. It is assumed that the SMA was pre-trained to curve upward along its entire length. Thus, together, deflections in portions 78C and 78D contribute to a much larger total deflection. FIG. 18 illustrates another possible resultant shape of layer 72 when sections 78B–D are heated and the SMA was pre-trained to assume an S-shape. Throughout the description it is understood that the SMA of sheet 72 can be trained before or after assembly. Training before assembly can be preferable when working with materials which would be damaged if trained together with the SMA, e.g., due to the high annealing temperatures.

Figure 19:
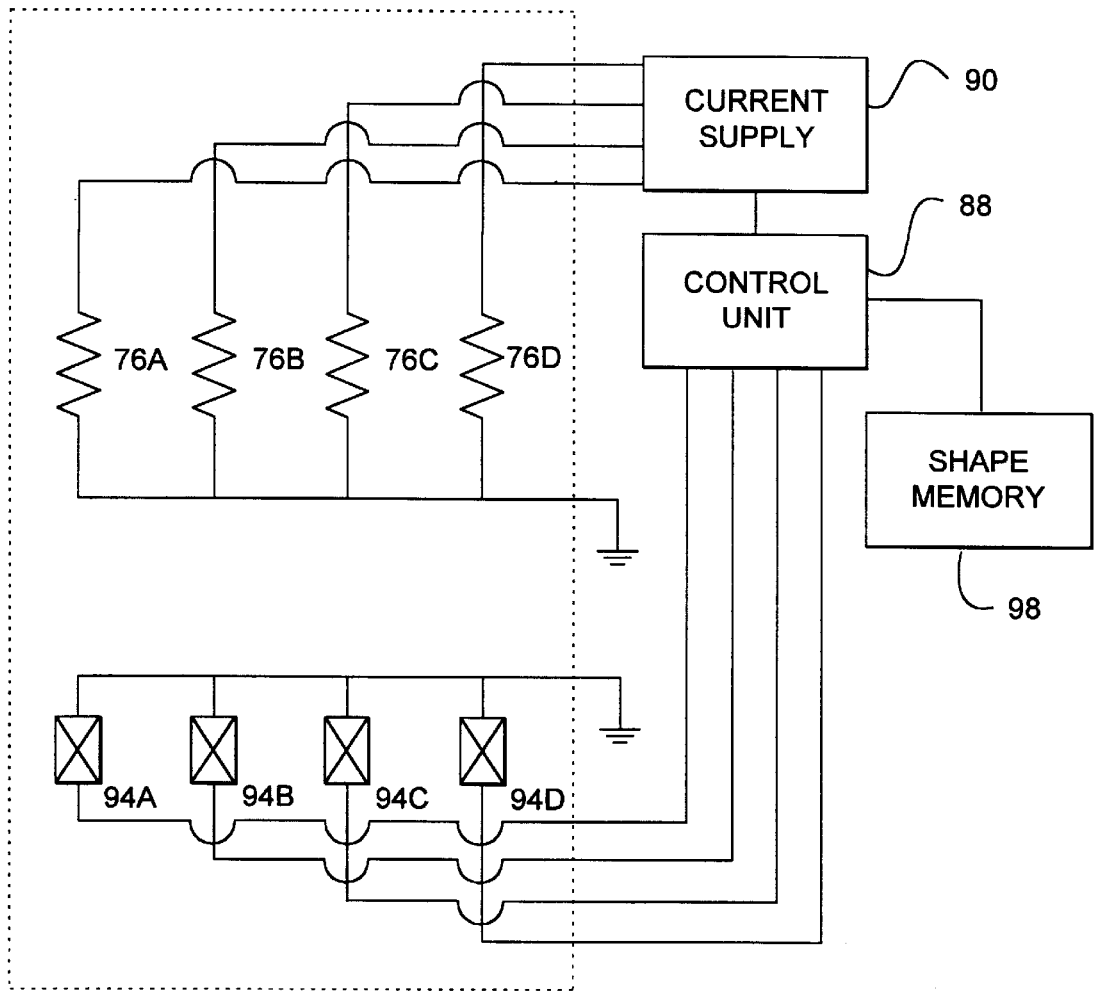
FIG. 19 is a diagram showing the equivalent circuit of an embodiment using deflection sensors.

The electrical diagram with sensors 94 is shown in FIG. 19. The dotted line represents elements mounted on sheet 72. While the connections to elements 76A–D remain the same, all sensors 94A–D are wired to control unit 88 via lines 96A–D respectively. In this manner unit 88 can receive signals representative of the local deflection from each one of sensors 94A–D individually. A shape memory 98 is connected to unit 88. Memory 98 is capable of mapping the resultant shape of sheet 72 based on information delivered from sensors 94A–D. Preferably, memory 98 has an inventory of resultant shapes produced by known combinations of elements 76. In other words, memory 98 is capable of recalling mapped resultant shapes positions and storing new ones. In the most preferred embodiment memory 98 can also store the actual current values corresponding to intermediate shapes of adjacent portions. This means that in operation shapes can be recalled and stored at will. The embodiment is thus highly versatile and practical for any diverse applications, e.g., guiding catheters.

Figure 20:
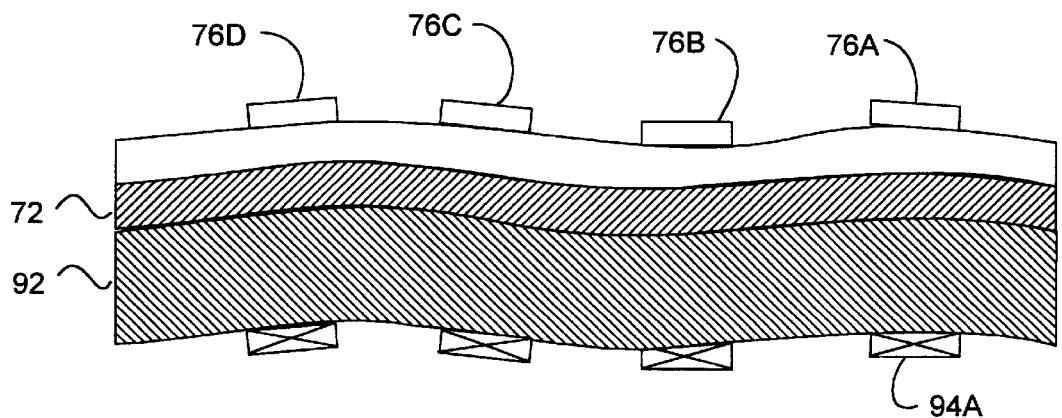
FIG. 20 is a cross-sectional view of a two-dimensional sheet with deflection sensors.

In another embodiment similar to the preferred embodiment sheet 72 has a coating layer 92 as shown in FIG. 20. For better understanding, the deflections in sheet 72 have been indicated. Deflection sensors 94A–D are positioned on layer 92. Sensors can be either angular deflections sensors, extension deflection sensors such as a strain gage, or bend sensors. A bend sensor is a strain gage disposed for measuring bending strain and thus angular deflection. All of these devices are well known in the art. In this case sensors 94A–D have been placed in locations corresponding to those of elements 76A–D. Depending on the geometry and application different placement may be preferable.

Figure 21:
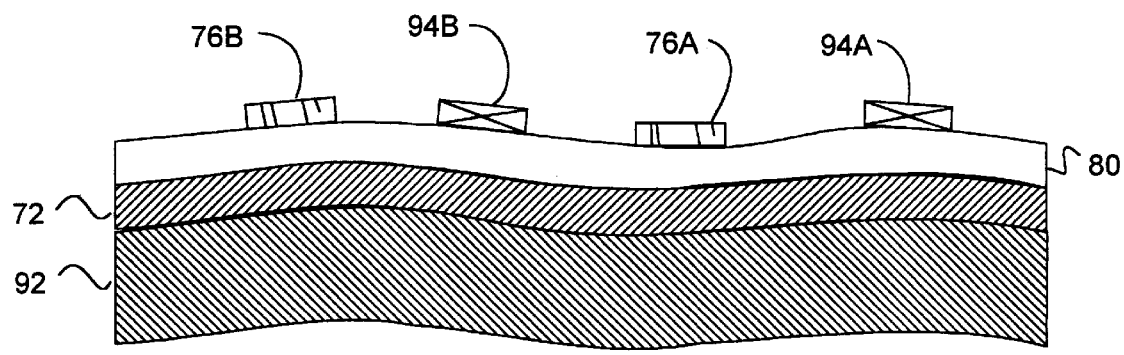
FIG. 21 is a cross-sectional view of a two-dimensional sheet with deflection sensors mounted next to heating elements.
Figure 22:
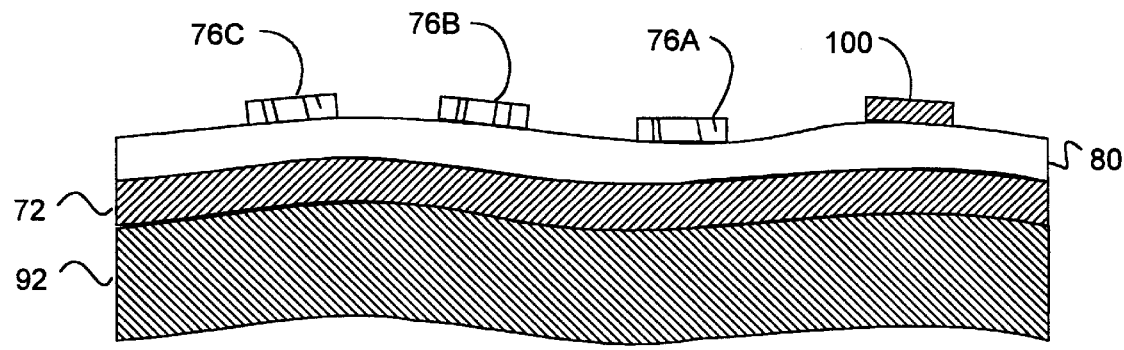
FIG. 22 is a cross-sectional view showing a two-dimensional sheet with a temperature sensor.

FIG. 21 shows yet another embodiment which differs from the above only in that sensors 94A–B are positioned between elements 76A–B. FIG. 22 shows another modification in which a temperature sensor 100 is mounted between elements. This is advantageous for monitoring the temperature of sheet 72. In a particularly preferred embodiment this data is stored in memory 98. Checking the temperature form sensor 100 during operation can prevent overheating and other related malfunctions. Of course, more than one thermal sensor 100 can be provided. Ideally, a number of such sensors 100 can be provided.

Figure 23:
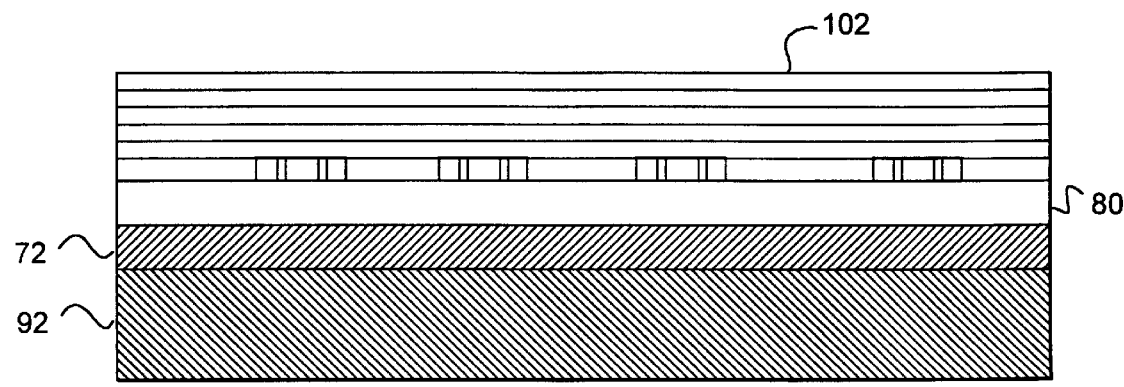
FIG. 23 is a cross-sectional view of a two-dimensional sheet with protective coating applied over the eating elements.

FIG. 23 shows the embodiment of FIG. 20 in the martensitic state encapsulated in a top coating layer 102. Layer 102 is applied to protect the electrical connections and elements in particular from damaging environmental factors, e.g., corrosive environments.

Figure 24:
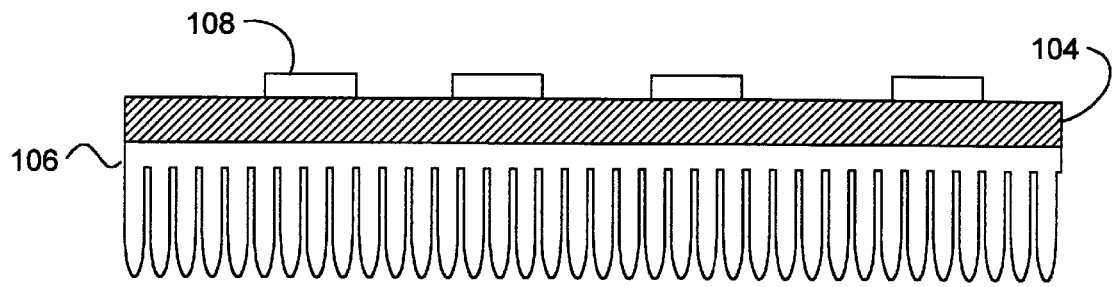
FIG. 24 is a cross-section of a two-dimensional sheet using vanes for heat dissipation.
Figure 25:
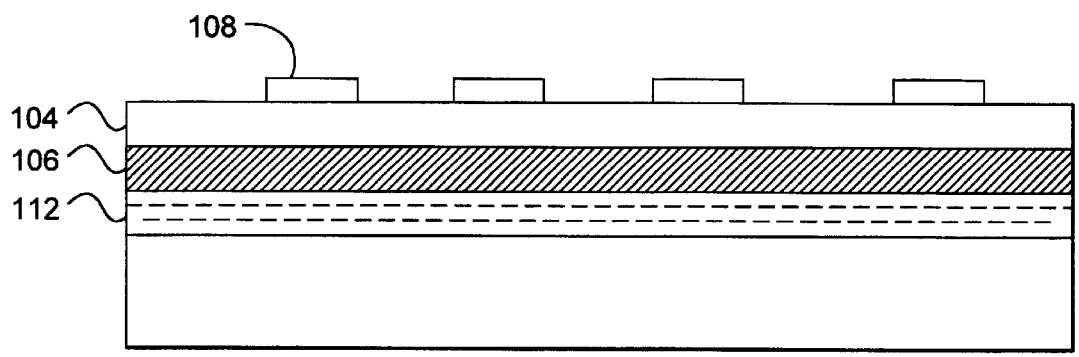
FIG. 25 is a cross-section of a two-dimensional sheet using water ducts for heat dissipation.

FIG. 24–FIG. 25 show two ways in which a two-dimensional sheet 104 of SMA can be cooled. For simplicity, all other elements, except for heating elements 108, have been omitted. In FIG. 24 the cooling element is a set of fins 106 in direct contact with sheet 104. This arrangement ensures efficient heat transfer and dissipation. Similarly, the structure in FIG. 25 efficiently dissipates heat using a substrate layer 110 with ducts 112 (only one shown). Ducts 112 carry a coolant, e.g., water, which absorbs and carries away the waste thermal energy.

While the invention has been described in connection with what is presently considered to be the most practical and preferred embodiments, it is to be understood that the invention is not limited to the disclosed embodiments, but on the contrary, is intended to cover various modifications and equivalent arrangements included within the spirit and scope of the appended claims. For example, a Peltier device could also provide an equivalent solution to heat dissipation. Therefore, persons of ordinary skill in this field are to understand that all such equivalent structures are to be included within the scope of the following claims.

What is claimed is:

1. A method for treating an aneurism, comprising:

providing a patch including a vessel interface side and an opposing non-interface side, the patch being formed of a sufficiently flexible material to provide a patch stowed state when the patch is delivered through the vessel and a patch deployed state when the patch is at least partially positioned over the mouth of the aneurism, the interface side of the patch being configured to form an adherence between the patch and an area of a vessel wall adjacent to the aneurism mouth, and wherein the patch includes an aperture for communication with the aneurism;

introducing the patch through the vessel in the stowed state;

positioning the patch at least partially adjacent to the aneurism so that the aperture is substantially adjacent to the mouth of the aneurism;

deploying the patch from the stowed state to the deployed state; and forming an adherence between the patch and an area of a vessel wall adjacent to the aneurism mouth.

2. The method of claim 1, wherein the adherence maintains a position of the patch relative to the aneurism.

3. The method of claim 1, further comprising:

applying a low pressure source to the aneurism through the aperture of the patch to evacuate the aneurism.

4. The method of claim 3, further comprising:

at least partially collapsing the aneurism.

5. The method of claim 1, further comprising:

delivering adhesion material to an area between the vessel wall and the interface surface of the patch at least partially after the patch is in the deployed state.

6. The method of claim 2, wherein the patch is passively activated from the stowed state to the deployed shape.

7. The method of claim 2, wherein the patch is actively deployed from the stowed state to the deployed shape.

8. The method of claim 2, wherein at least a portion of the patch is made of a material that provides passive deployment to the deployed state.

9. The method of claim 2, wherein at least a portion of the patch is made of a material that provides active deployment to the deployed state.

* * * * *